United States Patent [19]

Bacha et al.

[11] 4,003,800

[45] Jan. 18, 1977

[54] STYRENE PURIFICATION PROCESS

[75] Inventors: John D. Bacha; Charles M. Selwitz, both of Monroeville, Pa.

[73] Assignee: Gulf Research & Development Company, Pittsburgh, Pa.

[22] Filed: Jan. 2, 1976

[21] Appl. No.: 646,403

[52] U.S. Cl. .............................. 203/9; 260/669 A; 203/57; 203/62; 203/65
[51] Int. Cl.² ......................................... C07C 7/04
[58] Field of Search ................... 203/9, 57, 65, 62; 260/669 A

[56] References Cited

UNITED STATES PATENTS

| | | | |
|---|---|---|---|
| 2,399,340 | 4/1946 | Franz | 203/9 |
| 3,448,015 | 6/1969 | Rogers | 203/9 |
| 3,632,626 | 1/1972 | Schneller | 260/669 A |
| 3,654,129 | 4/1972 | Bloch | 203/9 |

*Primary Examiner*—Hiram H. Bernstein

[57] ABSTRACT

The present invention relates to the use of quinone alkides as polymerization inhibitors in a styrene purification process. The inhibitors are prepared by oxidizing hindered phenols to the corresponding quinone alkide.

3 Claims, No Drawings

STYRENE PURIFICATION PROCESS

FIELD OF THE INVENTION

This invention relates to a process for inhibiting the polymerization of styrene during the purification of crude styrene using a quinone alkide as the polymerization inhibitor.

Styrene is utilized extensively in the plastics industry for the manufacture of plastics, rubber-modified impact polystyrene, acrylonitrile-butadiene-styrene terpolymer, styrene acrylonitrile copolymer and in the production of styrenebutadiene type synthetic rubber.

DESCRIPTION OF PRIOR ART

The use of styrene polymerization inhibitors in the production of styrene monomer is known. For example, most of the styrene produced today is manufactured from ethylbenzene in a continuous dehydrogenation process using either the adiabatic cracking method or the isothermal method. The two methods differ only in the manner in which the heat necessary for the conversion of ethylbenzene to styrene is supplied.

The final step in styrene manufacture is the purification of styrene in the dehydrogenation reactor effluent. Vacuum distillation is commonly used to keep tower temperatures low and to minimize the polymerization of styrene. In addition, to further reduce styrene polymerization, inhibitors such as sulfur dioxide or dinitrophenols are introduced into the purification stills. In particular, U.S. Pat. No. 3,644,549, Innes et al, issued Feb. 22, 1972, relates to the production of styrene by the dehydrogenation of ethylbenzene using a ferrite catalyst and sulfur dioxide as an inhibitor, which is then carried through the purification stages.

Government regulations and restrictions concerning the use of sulfur compounds in reactions which may pollute the atmosphere have resulted in a search for other alternatives and compounds suitable for use in styrene manufacture. Dinitrophenol has been suggested as a substitute for sulfur dioxide in the production of styrene. The compound, however, is toxic, very difficult to store and presents a fire hazard.

As can readily be determined from the foregoing, various methods and polymerization inhibitors have been employed in the production and manufacture of styrene. There is, however, a continuous and ongoing search for newer, better and more economical methods for producing styrene monomer.

SUMMARY OF THE INVENTION

This invention relates to a method for inhibiting the polymerization of styrene monomer during processing thereof; the improvement which comprises a continuous mass process for preparing styrene, adding during said processing a polymerizing inhibiting amount of a quinone alkide, said quinone alkide having the formula:

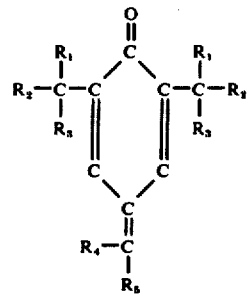

wherein $R_1$, $R_2$ and $R_3$ are either alike or different, members selected from the group consisting of hydrogen, straight or branched chain alkyl moieties having from 1 to 8 carbon atoms, phenyl and alkyl substituted phenyl moieties having up to 9 carbon atoms, cyclic hydrocarbon moieties having from 3 to 5 carbon atoms; and wherein $R_4$ and $R_5$ are either alike or different, members selected from the group consisting of hydrogen, straight-or branched chain alkyl moieties having from 1 to 18 carbon atoms, phenyl and alkyl substituted phenyl moieties having up to 9 carbon atoms, and cyclic hydrocarbon moieties having from 3 to 5 carbon atoms.

DETAILED DESCRIPTION OF PREFERRED EMBODIMENTS

The styrene purification process of the present invention can be carried out in a conventional manner, using conventional methods known in the art, with the exception that a quinone alkide is added to the purification zone of crude styrene monomer during the purification step of a mass or continuous production process.

A commercial method of manufacturing styrene monomer consists of dehydrogenating ethylbenzene to styrene by contacting the ethylbenzene under dehydrogenation conditions with a catalyst. The crude styrene which contains some impurities is next passed through a pot containing sulfur, where enough sulfur is dissolved to act as a styrene polymerization inhibitor. This styrene which is diluted with ethylbenzene, tar and sulfur is transported to a purification still, containing separation trays (e.g. a single column of approximately 70 plates) and is distilled under reduced temperature and pressure. The purified styrene is recovered from the overhead, while polystyrene, tars and sulfur compounds pass through the bottom portion of the distillate.

In accordance with the present invention, styrene is continuously mass produced in a dehydrogenation process of ethylbenzene in any type of reactor conventionally employed for a continuous mass styrene production process. For example, a reactor is charged with ethylbenzene under dehydrogenation conditions and crude styrene is recovered using air or water cooled condensers, or both. Before styrene is introduced to the purification still, a minor but polymerization inhibition amount of a quinone alkide substantially as described and claimed herein is charged to the purification zone. Crude styrene is then forwarded to the purification still, where the styrene is purified and concentrated by vacuum distillation to keep the still temperature low and minimize styrene polymerization.

In particular, it is desirable to maintain the still temperature below 105° C. and a total pressure drop in the still of 315 mm Hg or less. The purification step in the mass production of styrene can be conducted according to methods commonly employed in the art. One method consists of introducing the crude styrene into towers containing distillation sieve tower trays, the concept of which is described in U.S. Pat. No. 3,282,576 to Bruckert et al.

It should additionally be understood that the reaction temperature and pressure employed in the purification step of the process will fall within the range of temperatures and pressures customarily employed in the manufacture and purification of styrene monomer. For example, during the purification and concentration of styrene monomer, the purification still is normally operated at a temperature range of from about 90° C. to about 100° C. and under a vacuum of from about 160 mm Hg to about 315 mm Hg to reduce styrene polymerization and aid in the recovery of styrene monomer.

Quinone alkides which are suitable for use include:
2,6-di-t-butyl-4-methenyl quinone methide;
2,6-di-t-butyl-4-ethenyl quinone methide;
2,6-di-t-butyl-4-n-propenyl quinone methide;
2,6-di-t-butyl-4-isopropenyl quinone methide;
2,6-di-t-butyl-4-n-butenyl quinone methide;
2,6-di-t-butyl-4-isobutenyl quinone methide;
2,6-di-t-butyl-4-sec-butenyl quinone methide;
2,6-di-t-butyl-4-n-pentenyl quinone methide;
2,6-di-t-amyl-4-methenyl quinone methide;
2,6-di-t-amyl-4-ethenyl quinone methide;
2,6-di-n-dodecyl-4-methenyl quinone methide;
2,6-di-n-dodecyl-4-ethenyl quinone methide;
2,6-di-cyclopentyl-4-methenyl quinone methide;
2,6-di-cyclopentyl-4-ethenyl quinone methide;
2,6-di-cyclohexyl-4-methenyl quinone methide;
2,6-di-cyclohexyl-4-ethenyl quinone methide; or
2,6-di-phenyl-4-methenyl quinone methide.

The quinone alkides herein are preferably used in the purification step of the process in the amount of from about 25 ppm to about 1,000 ppm parts of styrene monomer in the purification still, preferably from about 50 ppm to 800 ppm parts of styrene monomer.

It should additionally be noted that the alkyl groups of the quinone alkides, as herein described, can be increased or decreased in size, thus effecting the compound molecular weight and boiling point. This is very important because the quinone alkides can be made to operate at various levels in towers containing distillation sieve tower trays by changing the alkyl carbon chain length of the compound.

Quinone alkides which are suitable for use herein are described in the copending application of Bacha et al, entitled "Quinone Alkide Synthesis System," Ser. No. 660,718, filed Feb. 23, 1976; and Bacha et al, entitled "Process for Inhibiting the Polymerization of Styrene," Ser. No. 646,399, filed Jan. 2, 1976.

The following examples serve to further illustrate and instruct one skilled in the art the best mode of how to practice this invention and are not intended to be construed as limiting thereof.

TABLE 1

| | | Styrene Polymerization Inhibition[a] | | |
|---|---|---|---|---|
| Run | Styrene gms. | Inhibitor[b] | Concentration of Inhibitor (ppm) | Time hrs. | Styrene Polymer gms. |
| 1 | 300 | Control | — | 3 | 31.5 |
| 2 | 300 | QE | 500 | 3 | 0.30 |
| 3 | 300 | QE | 250 | 3 | 2.25 |
| 4 | 300 | QE | 125 | 3 | 8.79 |
| 5 | 300 | QE | 500 | 5 | 1.38 |

TABLE 1-continued

| | | Styrene Polymerization Inhibition[a] | | |
|---|---|---|---|---|
| Run | Styrene gms. | Inhibitor[b] | Concentration of Inhibitor (ppm) | Time hrs. | Styrene Polymer gms. |
| 6 | 300 | QE | 500 | 7 | 5.44 |
| 7 | 300 | QNB | 1000 | 3 | 0.01 |
| 8 | 300 | QNB | 500 | 3 | 1.47 |
| 9 | 300 | QNB | 250 | 3 | 3.60 |
| 10 | 300 | QNB | 125 | 3 | 9.86 |
| 11 | 300 | QNB | 500 | 5 | 3.09 |
| 12 | 300 | QNB | 500 | 7 | 4.67 |
| 13 | 300 | QIP | 500 | 3 | 7.93 |
| 14 | 300 | QIP | 250 | 3 | 13.40 |
| 15 | 300 | QIP | 125 | 3 | 19.95 |
| 16 | 300 | QIP | 500 | 5 | 14.29 |
| 17 | 300 | QIP | 500 | 7 | 19.08 |
| 18 | 300 | QSB | 500 | 3 | 11.95 |
| 19 | 300 | QSB | 250 | 3 | 18.23 |

[a]Each run contained 300 g of styrene; the tests were conducted at 105° C. and 225 mm. Hg pressure.
[b]QE = 2,6-di-t-butyl-4-ethenyl quinone methide.
QNB = 2,6-di-t-butyl-4-n-butenyl quinone methide.
QIP = 2,6-di-t-butyl-4-isopropenyl quinone methide.
QSB = 2,6-di-t-butyl-4-sec-butenyl quinone methide.

A series of runs were conducted according to the concentrations and conditions set forth in Table I above. A tabulation of the results indicated that quinone alkides as herein defined effectively inhibit styrene polymerization during the insolation purification and separation of styrene monomers.

EXAMPLE I

Control

A 500 ml flask was charged with 300 g of styrene. Condenser connected to a vacuum system was joined to the flask, the system was flushed with dry nitrogen and the pressure reduced to 225 mm Hg. Such reduced pressure produces reflux at 105° C. The contents of the flask were heated at reflux for 3 hours; then the pressure was returned to atmospheric by the admittance of nitrogen. The contents of the flask were added to 500 ml. of methanol and vigorously shaken. After standing for 0.5 hour and cooling to about 25° C., the solution was vacuum filtered to separate the methanol insoluble polymer that had formed. Traces of methanol were removed by heating (90°–100° C) the separated polymer in a vacuum oven (315 mm Hg.) overnight. 31.5 gm of styrene polymer resulted from the isolation procedure.

EXAMPLE II

The procedure of Example I was followed with the following exception. 0.3 g (1000 PPM) of*2,6-di-t-butyl-4-ethenyl quinone methide was charged to the 500 ml flask with the styrene. Only 0.01 gm of styrene was converted to the polymer. * - In the above example 2,6-di-t-butyl-4-methenyl quinone methide, 2,6-di-t-butyl-4-n-propenyl quinone methide; 2,6-di-t-butyl-4-isobutenyl quinone methide; or 2,6-di-t-butyl-4-n-pentenyl quinone methide can be substituted for 2,6-di-t-butyl-4-ethenyl quinone methide with substantially the same results.

EXAMPLE III

The procedure described in Example I was repeated using 0.15 gm (500 PPM) of*2,6-di-t-butyl-4-isopropenyl quinone methide as the inhibitor. Analysis indicated that 7.93 gms of styrene polymerized. * - When 2,6-di-t-aryl-4-methenyl quinone methide or 2,6-di-t-aryl-4-ethenyl quinone methide is substituted for the 2,6-di-t-butyl-4-isopropenyl quinone methide above, substantially the same results are obtained.

EXAMPLE IV

A 500 ml flask was charged with 300 gms of styrene and 0.15 gm (500 PPM) of* 2,6-di-t-butyl-4-n-butenyl quinone methide. The procedure disclosed in Example I was followed with only 1.47 gms of styrene converted to the polymer. *-Substitution of 2,6-di-n-dodecyl-4-methenyl quinone methide or 2,6-di-n-dodecyl-4-ethenyl quinone methide for the 2,6-di-t-butyl-4-n-butenyl quinone methide above, gives substantially the same results.

EXAMPLE V

The procedure of Example I was repeated with the following exception. The 500 ml flask was charged with 0.15 gm (500 PPM) of* 2,6-di-t-butyl-4-sec-butenyl quinone methide. Analysis indicated 11.95 gms of styrene polymerized. *-The following compounds can be substituted for the 2,6-di-t-butyl-4-sec-butenyl quinone methide above with substantially the same results:
- 2,6-di-cyclopentyl-4-methenyl quinone methide;
2,6-di-cyclopentyl-4-ethenyl quinone methide;
2,6-di-cyclohexyl-4-methenyl quinone methide;
2,6-di-cyclohexyl-4-ethenyl quinone methide; or
2,6-di-phenyl-4-methenyl quinone methide.

We claim:
1. In a method for inhibiting the polymerization of styrene monomers during the vacuum distillation processing thereof, the improvement which comprises a continuous mass process for preparing styrene, adding during said vacuum distillation processing a polymerizing inhibiting amount of a quinone alkide, said quinone alkide having the formula:

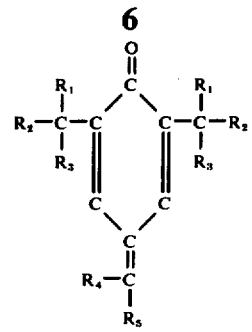

wherein $R_1$, $R_2$ and $R_3$ are either alike or different, members selected from the group consisting of hydrogen, straight or branched chain alkyl moieties having from 1 to 8 carbon atoms, phenyl and alkyl substituted phenyl moieties having up to 9 carbon atoms, cyclic hydrocarbon moieties having from 3 to 5 carbon atoms, and wherein $R_4$ and $R_5$ are either alike or different, members selected from the group consisting of hydrogen, straight or branched chain alkyl moieties having from 1 to 18 carbon atoms, phenyl and alkyl substituted phenyl moieties having up to 9 carbon atoms, and cyclic hydrocarbon moieties having from 3 to 5 carbon atoms.

2. The method according to claim 1 wherein the quinone alkide is selected from the group of:
2,6-di-t-butyl-4-methenyl quinone methide;
2,6-di-t-butyl-4-ethenyl quinone methide;
2,6-di-t-butyl-4-n-propenyl quinone methide;
2,6-di-t-butyl-4-isopropenyl quinone methide;
2,6-di-t-butyl-4-n-butenyl quinone methide;
2,6-di-t-butyl-4-isobutenyl quinone methide;
2,6-di-t-butyl-4-sec-butenyl quinone methide;
2,6-di-t-butyl-4-n-pentenyl quinone methide;
2,6-di-t-amyl-4-methenyl quinone methide;
2,6-di-t-amyl-4-ethenyl quinone methide;
2,6-di-n-dodecyl-4-methenyl quinone methide;
2,6-di-n-dodecyl-4-ethenyl quinone methide;
2,6-di-cyclopentyl-4-methenyl quinone methide;
2,6-di-cyclopentyl-4-ethenyl quinone methide;
2,6-di-cyclohexyl-4-methenyl quinone methide;
2,6-di-cyclohexyl-4-ethenyl quinone methide; or
2,6-di-phenyl-4-methenyl quinone methide.

3. The method according to claim 1 wherein the quinone alkide comprises from 25 ppm to 1000 ppm parts of styrene.

* * * * *

UNITED STATES PATENT AND TRADEMARK OFFICE
CERTIFICATE OF CORRECTION

PATENT NO. : 4,003,800
DATED : January 18, 1977
INVENTOR(S) : John D. Bacha and Charles M. Selwitz It is certified that error appears in the above-identified patent and that said Letters Patent are hereby corrected as shown below:

Col. 2, line 1 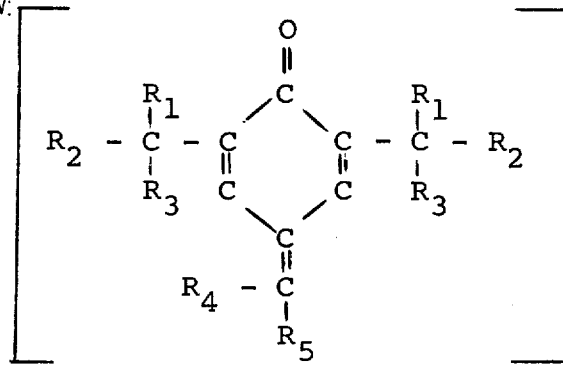 should read 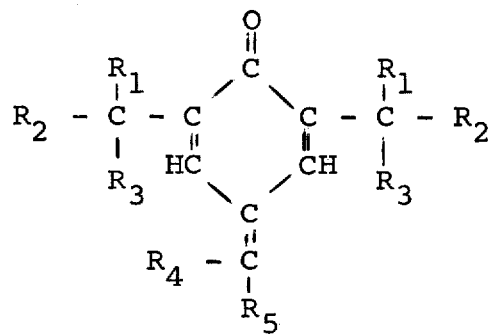

Col. 4, line 27 "insolation" should read -- isolation --.
Col. 4, line 33 "Condensor" should read --A condensor--.

UNITED STATES PATENT AND TRADEMARK OFFICE
CERTIFICATE OF CORRECTION

PATENT NO. : 4,003,800
DATED : January 18, 1977
INVENTOR(S) : John D. Bacha and Charles M. Selwitz It is certified that error appears in the above-identified patent and that said Letters Patent are hereby corrected as shown below:

Col. 6, line 1

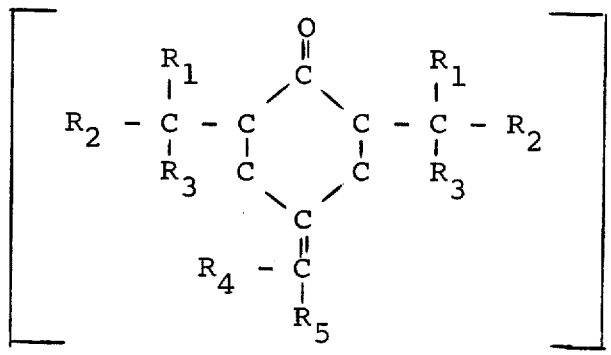

should read

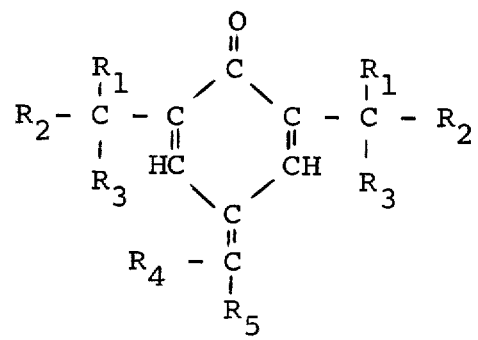

Signed and Sealed this

Twenty-eighth Day of June 1977

[SEAL]

Attest:

RUTH C. MASON
Attesting Officer

C. MARSHALL DANN
Commissioner of Patents and Trademarks